United States Patent [19]

Cochran

[11] 4,440,159

[45] Apr. 3, 1984

[54] VETERINARY APPLIANCE FOR USE ON A FRONT LEG OF A SMALL ANIMAL

[76] Inventor: Phillip E. Cochran, 4965 Barger Dr., Eugene, Oreg. 97402

[21] Appl. No.: 278,982

[22] Filed: Jun. 29, 1981

[51] Int. Cl.³ .............................................. A61F 5/04
[52] U.S. Cl. ..................................... 128/84 R; 128/88; 128/133
[58] Field of Search ...................... 128/75, 80 R, 80 A, 128/80 B, 80 C, 80 F, 83 R, 84 R, 84 A, 84 B, 84 C, 88, 89 R, 89 A, 133–134, 85; 128/87 R, 87 A, 87 B, 87 C; 273/188 R, 188 A, 189 R, 189 A; 119/96; 54/65, 82

[56] References Cited

U.S. PATENT DOCUMENTS

| | | | |
|---|---|---|---|
| 1,457,710 | 6/1923 | MacDonald | 128/80 C |
| 2,260,216 | 10/1941 | Doyle | 128/87 R |
| 2,744,526 | 5/1956 | Saylors . | |
| 2,816,525 | 12/1957 | Hoagland . | |
| 2,941,507 | 6/1960 | Becker et al. . | |
| 3,028,858 | 4/1962 | Cutler . | |
| 3,166,049 | 1/1965 | Lundin . | |
| 3,196,870 | 7/1965 | Sprecher et al. | 128/133 |
| 3,439,673 | 4/1969 | Sprecher . | |
| 3,454,002 | 7/1969 | Westlake et al. . | |
| 3,651,803 | 3/1972 | Bimler | 128/88 |
| 3,732,847 | 5/1973 | Andersen . | |
| 3,762,405 | 10/1973 | De George | 128/88 X |
| 3,812,851 | 5/1974 | Rodriguez | 128/89 R X |
| 3,878,842 | 4/1975 | Goldberg . | |
| 3,967,343 | 7/1976 | Westervelt et al. . | |
| 3,979,792 | 9/1976 | Prince et al. . | |
| 4,029,090 | 6/1977 | Dawson, Jr. . | |
| 4,099,525 | 7/1978 | McCarthy . | |
| 4,191,373 | 3/1980 | Lancellotti . | |
| 4,237,708 | 12/1980 | Bremer, Jr. . | |
| 4,323,059 | 4/1982 | Rambert et al. | 128/80 C |
| 4,336,796 | 6/1982 | Andrews et al. | 128/87 R |

FOREIGN PATENT DOCUMENTS 2447184  9/1980  France ............................. 128/80 C Primary Examiner—Kyle L. Howell
Assistant Examiner—Angela D. Sykes
Attorney, Agent, or Firm—Kolisch, Hartwell & Dickinson

[57] ABSTRACT

A veterinary appliance for use on a selected front leg of a small animal, such as a canine or feline, to isolate the leg includes a brace detachably mountable on the leg for limiting the extent to which the ulnar portion of the leg may be bent toward its associated humeral portion. The brace nonetheless permits substantially unconstrained movement of the leg to an extended position. Additionally, the brace includes a first section which is mountable on the ulnar portion and a second section connected thereto which is configured to engage the humeral portion and transfer a reactive force to the first section and correspondingly to the ulnar portion to prevent further bending toward the humeral portion after bending to a predetermined angular position has occurred.

9 Claims, 3 Drawing Figures

VETERINARY APPLIANCE FOR USE ON A FRONT LEG OF A SMALL ANIMAL

BACKGROUND AND SUMMARY OF THE INVENTION

The present invention relates to veterinary medicine, and more particularly to a novel device or appliance for use by a veterinarian in isolating and stabilizing the leg of a small animal, such as a canine or feline, in order to facilitate administration of fluid by intravenous feeding.

In the practice of veterinary medicine relating to small animals, it is common for a veterinarian to be confronted with caring for a dog or cat (*Canis familaris* or *Felis catus*) which has become sick or injured, necessitating intravenous feeding of the animal. For instance, dogs and cats can contract diseases which can lead to diarrhea, vomiting and shock and eventual death unless the animal is fed intravenously. Additionally, physically injured dogs and cats may become dehydrated or lapse into shock and the preferred treatment in replenishing fluids is through intravenous feeding.

Conventionally, the sick or injured animal is placed on a table in a so-called "pronated" position. This refers to the positioning of the animal with its head erect and front legs extended so that it paws face downwardly. The radio-ulnar portion (hereinafter called simply "ulnar" portion) of each of the front legs rest against the table and are bent relative to the upper or humeral portions. A tourniquet is then compressed around the humeral portion of a selected front leg so that distension of the cephalic vein occurs. That portion of the cephalic vein which extends along the ulnar portion of the leg is located by the veterinarian and a catheter is inserted thereinto. A tube connected to a bottle of suitable intravenous fluid is disposed above the animal, connected to the catheter, and the fluid is "dripped" into the cephalic vein so that it circulates into the cardiovascular system of the animal.

If the animal is particularly sick or injured, intravenous feeding over a period of several days may be required. In that case, it is necessary to prevent the animal from flexing or bending the ulnar portion of its leg (which is receiving the intravenous feeding) beyond a predetermined extent toward the humeral portion in order to ensure that blood flow through the cephalic vein does not become constricted. It is sometimes conventional veterinary practice to provide some type of brace or splint on the leg to maintain it in a fixed, unbendable position so that the animal may not flex its leg beyond some predetermined extent. When it is understood that intravenous feeding may occur over several days and that the animal will assume different lying positions tending to cause flexing, it can be seen that it is important to isolate the front leg so that such flexing does not occur beyond a predetermined extent.

However, there is a problem with conventional splints or braces because they do not permit the animal to stand with the leg being administered in an extended, standing position. As the animal tends to improve during intravenous feeding, it may wish to stand and walk around. With the selected leg in a bent position, maintained so by a brace or splint, it is impossible for the animal to extend its leg and it may injure itself if extension is attempted.

Another problem with conventional braces or splints for use on small animals resides in the fact that the brace must be taped onto the humeral portion of the animal's front leg to secure the brace thereon. The tape may constrict the cephalic vein which would interfere with the free flow of intravenous fluid being administered.

Accordingly, it is a general object of the present invention to provide a novel veterinary appliance for use on a selected front leg of a small animal, such as a canine or feline, which includes a brace means detachably mountable on the leg for limiting the extent to which the ulnar portion of the leg may be bent toward its associated humeral portion while, nevertheless, permitting substantially unconstrained movement of the leg to an extended position.

More particularly, it is an object of the present invention to provide an appliance, as described above, in which the brace means includes a first section mountable on and affixed to the ulnar portion and a second section connected thereto which is configured to engage the humeral portion and transfer a reactive force to the ulnar portion to prevent further bending of the ulnar portion toward the humeral portion after bending to a predetermined angular position has occurred. This construction permits a veterinarian to place a sick or injured dog or cat on a table in the pronated position, mount the brace means thereon, and administer intravenous feeding. Because the brace means of the present invention limits the extent to which the ulnar portion of the leg may be bent toward its associated humeral portion, preventing of constricting or occluding the cephalic vein is ensured. On the other hand, the animal may be permitted to extend its leg so that it may walk.

Another object of the present invention is to provide a veterinary appliance, as described above, in which the first and second sections are adjustable, relative to one another, so that the predetermined angular position sought to be limited between the ulnar and humeral portions may be selected as desired.

These and additional objects and advantages of the present invention will be more clearly understood after a consideration of the following drawings and the detailed description of the preferred embodiment.

DETAILED DESCRIPTION OF THE PREFERRED EMBODIMENT

Figure 1:
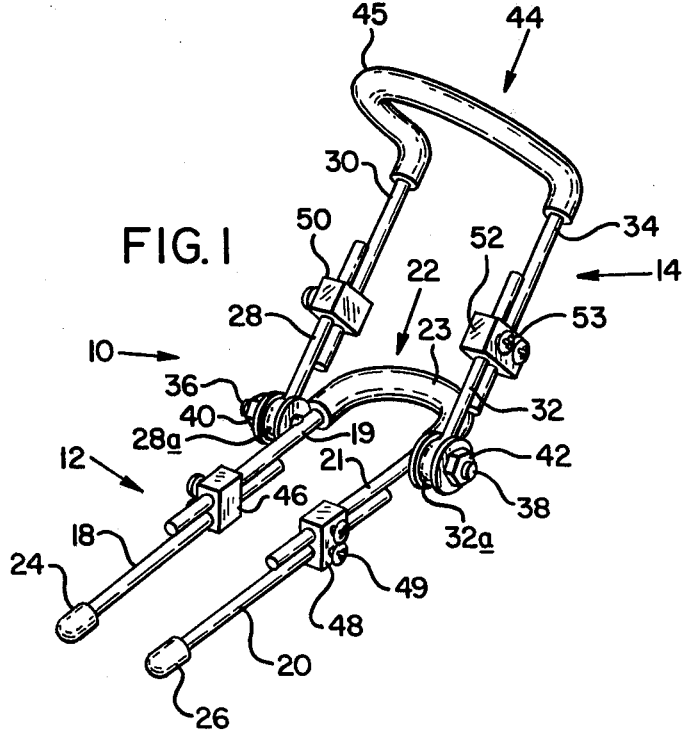
FIG. 1 is a perspective view of a veterinary appliance, according to the present invention for use on a small animal, shown isolated from the animal.

Reference is made initially to FIG. 1 of the drawings, which shows, in isolated perspective view, a veterinary appliance in accordance with the present invention generally indicated at 10. The appliance may be thought of as a brace means and includes two main components which will be characterized generally as a first section, generally indicated at 12, and a second section generally indicated at 14. It is contemplated that first section 12 will be mounted or positioned on the ulnar portion of a selected front leg of a small animal, such as a dog or cat, with second section 14 being disposed adjacent the humeral portion of the leg when the animal is in a pronated position. Appliance 10 is used to limit the extent to which the ulnar portion of the leg may be bent toward its associated humeral portion.

Figure 2:
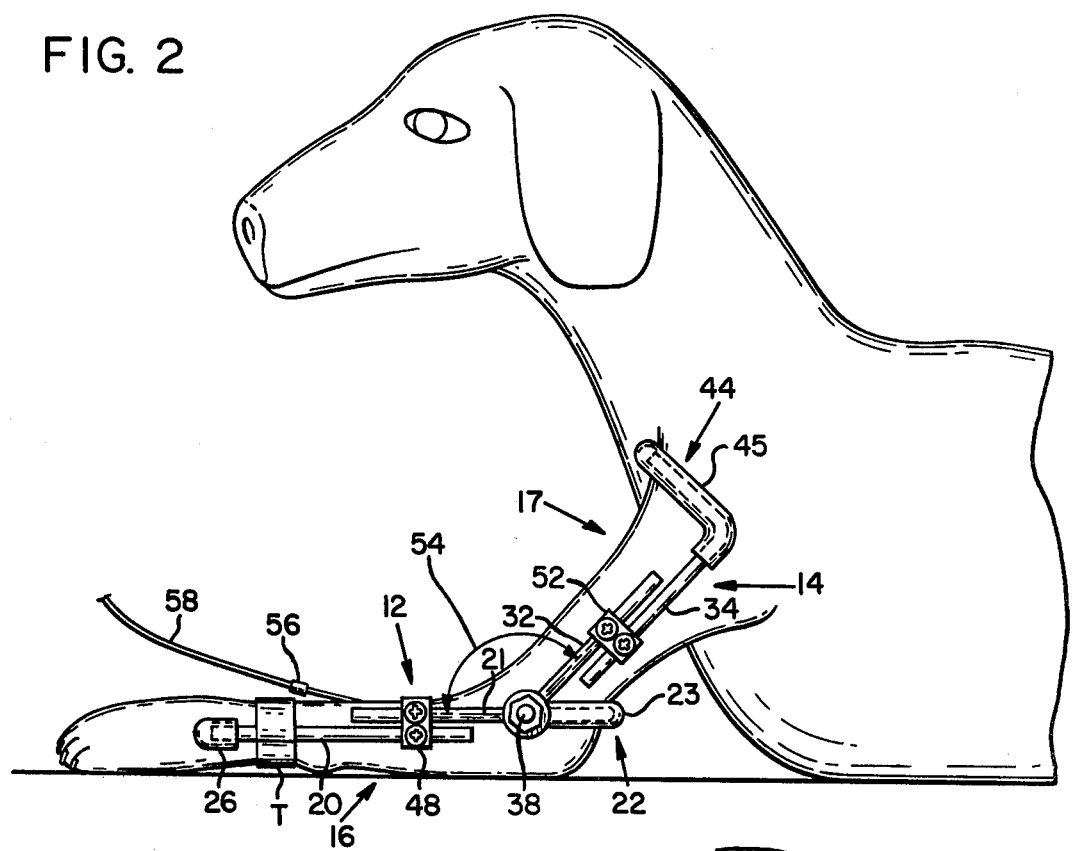
FIG. 2 is a side view of a small animal, such as a canine, showing mounting of the veterinary appliance on a selected front leg thereof during intravenous feeding.

As shown in FIG. 2, it can be seen that a small animal, such as a dog, is positioned on a veterinarian's treatment table or other flat surface. A selected front leg of the dog, such as its left leg, is bent and is shown in a pronated position or that position in which the paw faces downwardly with the dog lying on its stomach. Appliance 10 is shown with first section 12 being mounted adjacent the front or ulnar portion of the left leg, indicated at 16. The humeral portion of the dog's leg is indicated at 17. First section 12 includes first elongated means, such as parallel pairs of elongate members 18, 19 and 20, 21 (see FIG. 1) which are dimensioned to extend alongside the ulnar portion of the leg approximately from the region of the leg corresponding to the carpus (wrist) to the olecranon (elbow). Elongate members 18, 19 and 20, 21 are laterally-spaced apart and extend alongside the ulnar portion. Elongate members 19 and 21 extend at one set of their ends into a retaining means generally indicated at 22. As can be more clearly seen from a consideration of FIG. 1, retaining means 22 is dimensioned for positioning around a rear or posterior region of the humeral portion just above the olecranon. The olecranon of the dog, which may be thought of as the dog's elbow, is that eminence or projection situated at the upper and back of the ulna which is curved forward at its summit so as to present a prominent tip. Retaining means 22, (which may include a pad 23) is configured as a first arcuate member extending from elongate members 19, 21, for encircling the posterior region of the humeral portion above the olecranon, for resting thereon, and serves to orient first section 12 in proper position.

As shown in FIG. 2, tape, such as conventional adhesive tape, indicated at T, is used to affix or attach first section 12 to ulnar portion 16 of the animal. The tape may be suitably wrapped around elongate members 18, 20 adjacent the carpus of the animal's front leg. As also shown in FIG. 1, rubber tips or caps such as indicated at 24, 26 may be disposed on ends of elongate members 18, 20 so that a nonsharp surface adjacent the forward ends of elongate members 18, 20 is provided.

Considering now details of construction of second section 14, it can be seen that it includes second elongate means for extending upwardly from first section 12 such as interconnected pairs of elongate members 28, 30 and 32, 34. Elongate members 28, 32 are provided with loops at end portions thereof, such as loops 28a, 32a for receiving threaded pins 36, 38 which extend outwardly from elongate members 19, 21, respectively, of first section 12. Suitable nuts, such as indicated at 40, 42 may be used to tighten or clamp elongate members 28, 32 to any preselected angular orientation relative to elongate members 19, 21, and hence, the angular orientation of second section 14 may be selectively adjusted relative to first section 12. Thus, it can be appreciated that an orienting means has been provided which is manually adjustable for selectively varying the angular orientation between the first and second sections.

Continuing with a discussion of second section 14, it can be seen from a consideration of FIG. 1 that an engagement means, indicated at 44, (which may include a pad 45) is provided on the second section configured for positioning or abutting against an anterior region of humeral portion 17 when mounted on the animal as shown in FIG. 2. More particularly, it can be seen that engagement means 44 is formed as a second arcuate member for encircling an anterior part of the humeral portion when positioned thereagainst. As can be seen from a consideration of FIG. 2, the long axis of engagement means 44 is mounted generally at right angles to elongate members 30, 34.

Rounding out a description of the appliance, it is to be noted that first adjusting means, indicated at 46, 48 are provided for enabling selective longitudinal positioning of elongate members 18, 19 and 20, 21 respectively. Adjusting means 46, 48 are conventional blocks which are bored for receiving associated elongate members in side-by-side relationship and for affixing them by means of screws 49 in preselected position. Similarly, second adjusting means such as indicated at 50, 52 are provided for enabling selective positioning of elongate members 28, 30 and 32, 34 respectively.

Turning now to a description of the manner in how appliance 10 may be advantageously used in intravenous feeding, it is initially presumed that a sick or injured small animal, such as the dog shown in FIG. 2, is placed on a table or other surface in a veterinarian's office in the pronated position as shown. The veterinarian may preselect the angular orientation between first and second sections 12, 14, based on the size and anatomy of the dog, and has tightened nuts 40, 42 to a predetermined angular position. This will generally correspond to that angular orientation between ulnar portion 16 and humeral portion 17 assumed by the dog when it is in a comfortable pronated position as shown in FIG. 2. The relative positions of the elongate members of first and second sections 12, 14 respectively, are also preselected depending on the length dimension of the ulnar and humeral portions of the dog. The veterinarian then extends the dog's paw through the opening provided between the engagement means 44 and moves appliance 10, relative to the dog's leg, until retaining means 22 is positioned over the olecranon of the leg.

At this point, elongate members 18, 19 and 20, 21 should be positioned alongside the length of the ulnar portion 16. It may be necessary to adjust first adjusting means 46, 48 so that end caps 24, 26 are adjacent the carpus or wrist of the dog. It may now be noted whether or not engagement means 44 specifically abuts against or encircles an anterior part of humeral portion 17. Loosening of nuts 40, 42 may be necessary in order to dispose engagement means 44 against humeral portion 17. It may also be desired to position engagement means 44 adjacent the actual shoulder of the dog and to this end, second adjusting means 50, 52 may be suitably loosened so that elongate members 30, 34 may be shifted relative to elongate members 28, 32, respectively, on second section 14. When engagement means 44 is disposed against humeral portion 17 as desired, nuts 40, 42 are tightened to orient second section 14 to first section 12. The angle between elongate members 19, 28 and 21, 32 will be referred to as a predetermined angular position indicated at 54. Adhesive tape may then be wrapped around the dog's ulnar portion, adjacent the carpus, around elongate members 18, 20 to affix securely first section 12 to the ulnar portion. Of course, as mentioned above, retaining means 22 has been positioned slightly above the olecranon so that the prominence of the olecranon extends beneath retaining means 22 as shown in FIG. 2.

The veterinarian may now apply a tourniquet (this may have been done previously) to the humeral portion to distend the cephalic vein. A catheter is then inserted into the cephalic vein to provide intravenous feeding. A catheter and tube leading to a bottle of fluid (not shown) are indicated at 56, 58, respectively.

Figure 3:
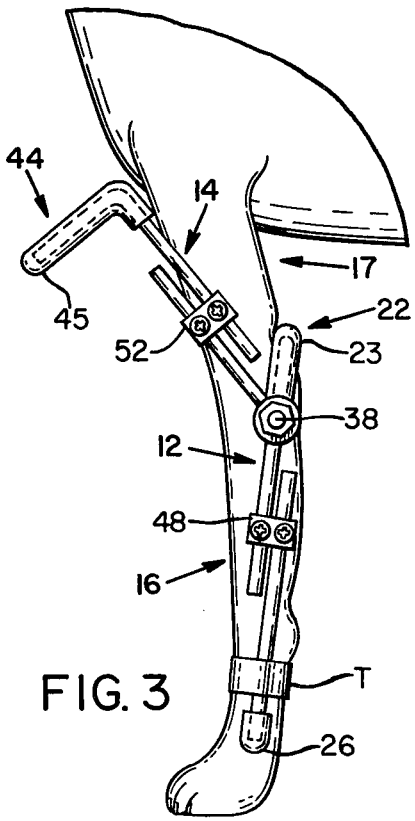
FIG. 3 is a view similar to FIG. 2 showing how the veterinary appliance of the present invention permits the animal to stand and extend the leg on which the appliance is mounted.

As mentioned previously, the animal's sickness or injuries may necessitate intravenous feeding over a period of days. If this is the case, the animal may wish to stand and even walk as it gains strength. Appliance 10 of the present invention provides an important advantage in that it actually permits substantially unconstrained movement of the selected leg, to which intravenous feeding is being directed, to be disposed to a substantially straightened or extended position as shown in FIG. 3. More particularly, FIG. 3 shows a dog in a standing position and it can be seen that with its left leg extended, second section 14 has been swung or pivoted, relative to humeral portion 17 forwardly so that engagement means 44 no longer abuts against the humeral portion. Because retaining means 22 is disposed above the olecranon, the prominence of the olecranon keeps first section 12 from falling rearwardly or working loose from its engagement with ulnar portion 16. Of course, it can also be seen that caps 24, 26 are disposed above the ground surface so that the dog's paw is free to contact the ground and permit relatively unimpeded walking with its leg in an extended position.

However, should the dog lie down on either of its sides, or assume any other position, it would be unable to bend or flex the ulnar portion of its leg beyond a limited extent toward the humeral portion. The predetermined angular position, which had been previously preselected and fixed, prevents the dog from bending to its leg to some extent less than the predetermined angular position. For instance, as the leg is moved from its extended position shown in FIG. 3 to a more flexed position, eventually engagement means 44 will engage or abut against an anterior part of humeral portion 17. When this occurs, it can be seen that second section 14, with engagement means 44 engaging the humeral portion, transfers a reactive, resistive force to first section 12 and correspondingly to ulnar portion 16. Further bending of ulnar portion 16 toward humeral portion 17 is prevented after bending to the predetermined angular position. Of course, the animal may extend its leg and return it to the predetermined angular position as often as it likes. After the required time period for intravenous feeding, the tape may be removed so that appliance 10 may be quickly detached.

The primary purpose behind using appliance 10 resides in preventing or limiting the extent to which the animal may flex its leg so that the cephalic vein does not become constricted. However, it should also be noted that it is desirable to fix the leg in some preselected position when the animal is pronated which ensures that the ulnar portion is disposed somewhat forwardly of the animal's head, as shown in FIG. 2. It has been found that the optimal predetermined angular position, represented by numeral 54, should be in the general range of 135°. By using such an orientation as a general guideline, subject of course to some variance, the veterinarian knows that the leg is positioned forwardly a sufficient extent, when the animal is in the pronated position, so that the ulnar portion is not completely beneath the animal's head. The veterinarian, therefore, has sufficient maneuvering room to locate the cephalic vein, shave the leg and insert the catheter.

The appliance of the present invention provides several important and distinct advantages. First of all, it provides the basic function of aiding a veterinarian in administering intravenous feeding to the leg of a small animal by isolating that leg and preventing or limiting the extent to which the ulnar portion may be bent toward its associated humeral portion. This prevents flexion which may cut off flow of the intravenous fluid through the cephalic vein. Additionally, as shown and described above, it can be appreciated that the appliance permits substantially unconstrained movement of the leg to an extended position.

While the present invention has been shown and described with reference to the foregoing preferred embodiment, it will be appreciated by those skilled in the art that other changes in form and detail may be made therein without departing from the spirit and scope of the appended claims.

It is claimed and desired to secure by Letters Patent:

1. A veterinary appliance for use on a selected front leg of a small animal, such as a canine or feline, comprising:

brace means adapted to be detachably mountable on the leg for limiting the extent to which the ulnar portion of the leg may be bent towards its associated humeral portion and for permitting substantially unconstrained movement of the leg to an extended position, said brace means including a first section mountable on the ulnar portion and a second section connected thereto configured to engage the humeral portion and transfer a reactive force to said first section and correspondingly to the ulnar portion to prevent further bending of the ulnar portion toward the humeral portion after bending to a predetermined angular position, said first section further including elongate means affixed to the ulnar portion including retaining means provided thereon for positioning around a posterior part of the humeral portion above the olecranon of the leg, and said second section including engagement means configured for abutting against an anterior part of the humeral portion when the ulnar portion has been bent, relative to the humeral portion, to said predetermined angular position.

2. The veterinary appliance of claim 1 wherein said elongate means is dimensioned to extend alongside the ulnar portion generally from the region of the leg corresponding to the carpus to the olecranon, said retaining means being defined by a first arcuate member extending from said elongate means for encircling the aforementioned posterior part of the humeral portion above the olecranon.

3. The veterinary appliance of claim 2 wherein said engagement means is defined by a second arcuate member for encircling the aforementioned anterior part of the humeral portion when abutted thereagainst.

4. A veterinary appliance for use on a selected front leg of a small animal, such as a canine or feline, comprising:

brace means including a first section adapted to be detachably mountable on the ulnar portion of the leg and a second section connected thereto configured to engage the associated humeral portion and transfer a reactive force to said first section and correspondingly to the ulnar portion to prevent further bending to a predetermined angular position, orienting means associated with said brace means selectively adjustable for varying said predetermined angular position, said first section including elongate means affixed to the ulnar portion including retaining means provided thereon for positioning around a posterior part of the humeral portion above the olecranon of the leg, and said second section including engagement means configured for abutting against an anterior part of the humeral portion where the ulnar portion has been bent, relative to the humeral portion, to said predetermined angular position.

5. The veterinary appliance of claim 4 wherein said elongate means is dimensioned to extend alongside the ulnar portion generally from the region of the leg corresponding to the carpus to the olecranon, said retaining means being defined by a first arcuate member extending from said elongate means for encircling the aforementioned posterior part of the humeral portion above the olecranon.

6. The veterinary appliance of claim 5 wherein said engagement means is defined by a second arcuate member for encircling the aforementioned anterior part of the humeral portion when abutted thereagainst.

7. The veterinary appliance of claim 6 further including adjusting means for enabling selective longitudinal positioning of said elongate means.

8. The veterinary appliance of claim 7 wherein said second section further includes additional elongate means for extending alongside the humeral portion.

9. The veterinary appliance of claim 8 further including additional adjusting means for enabling selective longitudinal positioning of said additional elongate means.

* * * * *